United States Patent [19]

Rawat et al.

[11] Patent Number: 5,688,258
[45] Date of Patent: Nov. 18, 1997

[54] DISPOSABLE COVER FOR AN ABSORBENT MATERIALS

[75] Inventors: Digvijay Rawat, Kobe, Japan; Carlos Jose Barroso, Maineville, Ohio; Letha Margie Hines, Cincinnati, Ohio; Peter Morris, Cincinnati, Ohio; Robb Eric Olsen, Cincinnati, Ohio; J. Alvaro Restrepo, Caracas, Panama; Nona Jane Redwine, Mason, Ohio; Mark Donovan Seymour; Hiroaki Shikata, both of Kobe, Japan

[73] Assignee: The Procter & Gamble Company, Cincinnati, Ohio

[21] Appl. No.: 504,870

[22] Filed: Jul. 20, 1995

Related U.S. Application Data

[63] Continuation-in-part of Ser. No. 432,659, May 2, 1995.

[51] Int. Cl.$^6$ .......................... A61F 13/15; A61F 13/20
[52] U.S. Cl. .................. 604/385.1; 604/393; 604/397; 604/402; 604/358; 604/378
[58] Field of Search ....................... 604/358, 369, 604/372, 370, 378, 385.1, 386, 393, 397–398, 401, 402

[56] References Cited

U.S. PATENT DOCUMENTS

| | | |
|---|---|---|
| 3,814,100 | 6/1974 | Nystrand et al. . |
| 3,828,784 | 8/1974 | Zoephel . |
| 3,929,135 | 12/1975 | Thompson . |
| 3,970,087 | 7/1976 | Castaneda . |
| 4,195,634 | 4/1980 | DiSalvo et al. . |
| 4,535,020 | 8/1985 | Thomas et al. . |
| 4,601,717 | 7/1986 | Blevins . |
| 4,690,679 | 9/1987 | Mattingly, III et al. . |
| 4,846,813 | 7/1989 | Raley ........................ 604/378 |
| 4,865,597 | 9/1989 | Mason, Jr. et al. ............. 604/385.1 |
| 4,973,325 | 11/1990 | Sherrod et al. .................. 604/378 |
| 5,135,521 | 8/1992 | Luceri et al. . |
| 5,219,342 | 6/1993 | Hatch et al. . |
| 5,268,224 | 12/1993 | DesMarais et al. . |
| 5,269,776 | 12/1993 | Lancaster et al. . |
| 5,277,954 | 1/1994 | Carpenter et al. . |
| 5,429,627 | 7/1995 | Johnson et al. . |
| 5,429,631 | 7/1995 | Grenier .......................... 604/358 |

FOREIGN PATENT DOCUMENTS

| | | |
|---|---|---|
| 0 319 314 A3 | 6/1989 | European Pat. Off. . |
| 30 13 913 A1 | 10/1981 | Germany . |
| 2 189 993 | 11/1987 | United Kingdom . |
| WO 86/06623 | 11/1986 | WIPO . |
| WO 91/16871 | 11/1991 | WIPO . |

*Primary Examiner*—P. Zuttarelli
*Attorney, Agent, or Firm*—Edward J. Milbrada; Steven W. Miller; Jeffrey V. Bamber

[57] ABSTRACT

A disposable cover which, when used with an absorbent material, such as a pad of woven cloth, provides an absorbent article, such as a catamenial pad is disclosed. In a preferred embodiment, the disposable cover comprises a liquid pervious rewet barrier and an anti-stain barrier joined thereto. Preferably, the rewet barrier comprises a material having capillaries which allow bodily liquids to rapidly penetrate therethrough and the anti-stain barrier is provided in two portions, one of which is joined to each longitudinal edge of the fewer barrier. The disposable cover can also be provided with absorbent attachment means for securing the cover to the absorbent material and with garment attachment means for securing the assembly of the disposable cover and the absorbent material to a user's undergarment. Alternative embodiments of the invention can assume a pouch configuration. This alternative configuration is particularly useful if the absorbent material is in a form lacking significant cohesiveness, such as a tow of fibers.

25 Claims, 4 Drawing Sheets

DISPOSABLE COVER FOR AN ABSORBENT MATERIALS

This is a continuation-in-part of application Ser. No. 08/432,659, filed on May 2, 1995 which is now pending as application Ser. No. 08/713,943, filed on Sep. 13, 1996.

FIELD OF THE INVENTION

The present invention relates to a disposable cover for an absorbent material, the combined structure serving as an absorbent article, such as a diaper, an incontinent pad, a sanitary napkin, or the like.

BACKGROUND OF THE INVENTION

Absorbent articles are designed to receive and retain fluid discharges from the body within an absorbent element of the absorbent article. In recent times, single use disposable absorptive devices have been improved to provide enhanced performance for the user and have replaced durable absorbent articles which are designed to be laundered and reused.

For all these improvements to disposable absorbent articles, launderable absorbent articles, such as woven cloth, are still preferred among certain users because of perceived cost effectiveness to the consumer or other reasons, despite the fact that such articles may be less comfortable to wear. Such discomfort is due to the fact that there is incomplete transfer of bodily fluids from a wearer's body into the absorbent article leaving the wearer wet and soiled. Another principle disadvantage of a launderable, woven cloth absorbent article is the fact that the user's clothing, for example an undergarment, can become stained if a woven cloth article becomes saturated with absorbed fluids. Users of rudimentary disposable absorbent articles, such as cotton wadding or tows of other fibers, suffer from the same performance deficiencies.

In order to minimize the effect of prolonged liquid contact with the skin, disposable absorbent articles have been produced with a body-contacting topsheet designed to exhibit a greater degree of surface dryness. Commercially available disposable absorbent articles have also been provided with a fluid impermeable backsheet for minimizing staining of a user's clothing by providing a barrier between the absorbent portions of the disposable absorbent article and the user's clothing. While such improved body-contacting topsheets and fluid impermeable backsheets of disposable absorbent articles provide commercially available disposable absorbent articles with improved functionality, those users who may choose to use a woven cloth absorbent article do not receive the benefit of this improved functionality.

Therefore, it is an object of the present invention to provide a disposable cover that may easily applied to a lauderable absorbent material such as a woven cloth pad or other kinds of rudimentary absorbent articles. It is a further object of this invention that the disposable cover provide improved functionality to a user by reducing liquid contact with the skin, minimizing the risk of stains to a user's clothing, and by helping maintain the absorbent material in a configuration suitable for absorbing bodily liquids. It is also an object of this invention to provide a disposable cover having such improved functionality for users of launderable absorbent materials at a cost that is low enough to be attractive to users of such launderable absorbent materials.

SUMMARY OF THE INVENTION

The disposable cover of this invention comprises a liquid pervious rewet barrier joined to a liquid impervious anti-stain barrier. Preferably, the liquid pervious rewet barrier comprises a nonwoven or a film material provided with capillaries penetrating through the thickness thereof to permit flow of fluid from the portion of the outwardly oriented surface of the rewet barrier which contacts a user's body, through the rewet barrier, to the inwardly oriented surface thereof for absorption by an absorbent material. The anti-stain barrier preferably comprises a thin, liquid impervious plastic film. In a preferred embodiment of the present invention, the rewet barrier and the anti-stain barrier are joined along at least one of their longitudinal edges. Preferably, the preferred embodiment of the present invention further comprises absorbent securement means disposed on the inwardly facing surface of the anti-stain barrier and garment securement means disposed on the outwardly facing surface of the anti-stain barrier.

In alternative embodiments of the present invention, the rewet barrier and the anti-stain barrier are joined on three sides to form a covering pouch that is suitable for containing an absorbent material comprising a fibrous assembly, such as a tow of fibers. Preferably, such alternative embodiments further comprise an acquisition layer joined to the rewet barrier. When such covering pouches are used, the acquisition layer is positioned between the rewet barrier and the absorbent material.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
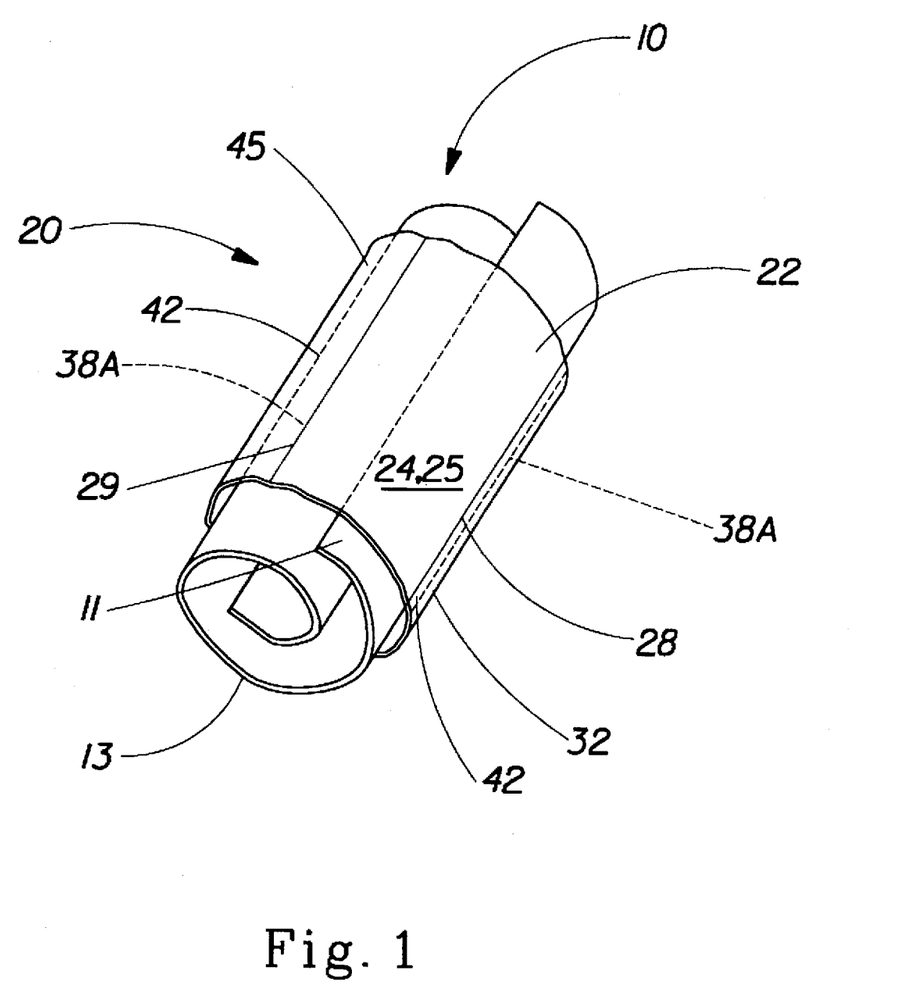
FIG. 1 is a perspective view of the disposable cover embodiment of the present invention in a typical in-use configuration as it would be applied by a user, the surface facing the viewer being the surface that is positioned adjacent the user's body.

As used herein, the term "absorbent article" refers to devices which absorb and contain body exudates, and, more specifically, refers to devices which are placed in proximity to the body of the user to absorb and contain the various exudates discharged from the body. A preferred embodiment of the present invention, is the disposable cover 20 for an absorbent material 10, the combined system having use as an absorbent article such as a catamenial pad, as is shown in FIG. 1. As used herein, the term "catamenial pad" refers to an absorbent article which is worn by females adjacent to the pudendal region, generally external to the urogenital region, and which is intended to absorb and contain menstrual fluids and other vaginal discharges from the user's body (e.g., blood, menses, and urine). As used herein, the term "pudendal" refers to the externally visible female genitalia. It should be understood, however, that the present invention is also applicable to other absorbent articles such as incontinence pads, diapers, and the like.

Figure 2:
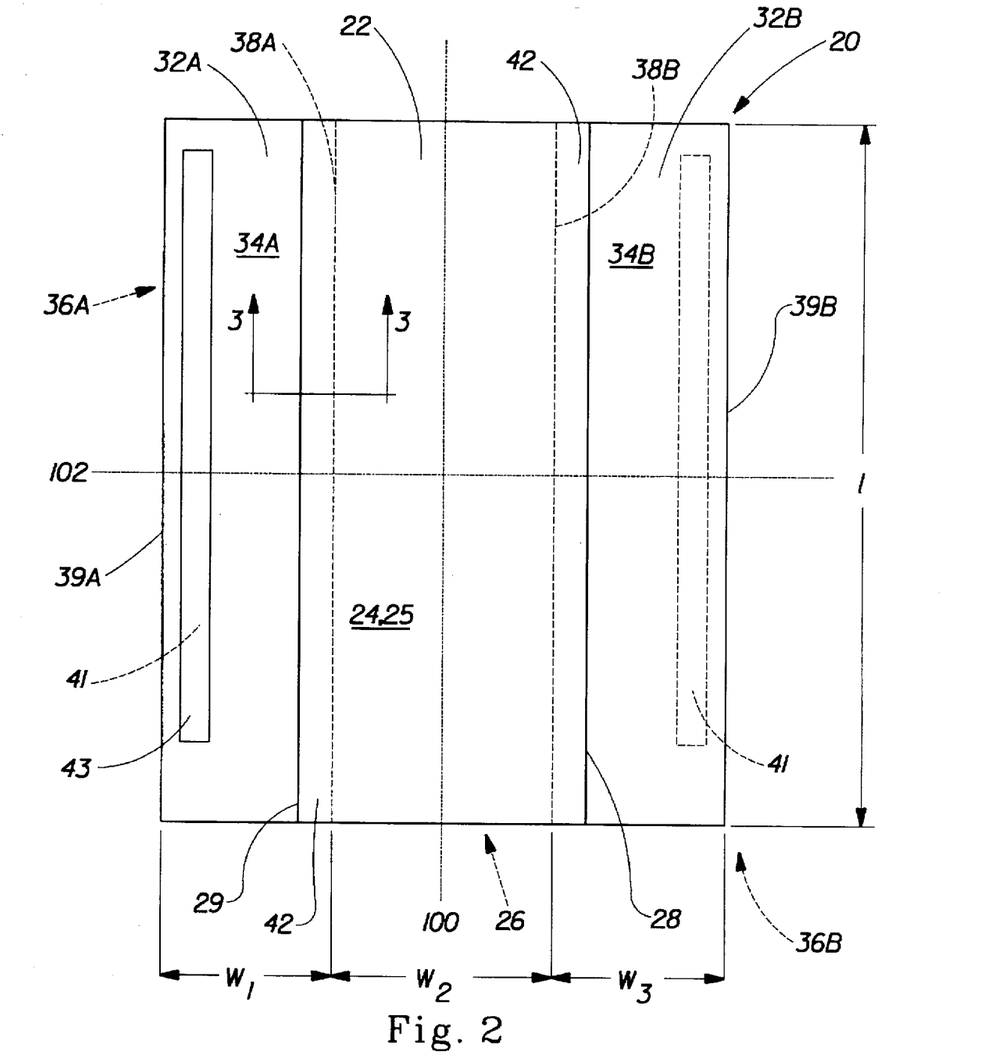
FIG. 2 is a plan view of the disposable cover embodiment of the present invention in an unfolded condition, the outwardly facing surface of the rewet barrier facing the viewer.

As can be seen in FIG. 1, the disposable cover 20 of the present invention wraps around the absorbent material 10 and covers it. The disposable cover 20 of the present invention is preferably joined to the absorbent material 10 by the absorbent securement means 41 (shown in FIG. 2), although such joinder is not necessary. The disposable cover 20 is preferably compliant, soft feeling, and non-irritating to the users' skin. The disposable cover comprises a liquid pervious rewet prevention component or rewet barrier 22 that permits bodily liquids (e.g., menses and/or urine) to readily penetrate through its thickness and reduces the tendency of such liquids to flow back through the rewet barrier 22 toward a user's skin. A preferred embodiment of the liquid pervious rewet barrier 22 can be formed from a liquid impermeable material by providing the impervious material with capillaries penetrating through the thickness thereof. The capillaries permit transportation of bodily exudates through the thickness of the fewer barrier 22 for transfer of bodily discharges into the absorbent material 10. The absorbent cover 20 further comprises a liquid impervious anti-stain barrier 32 that is preferably joined to the liquid pervious rewet barrier 22 along at least one longitudinal edge thereof. Preferably, as shown in FIG. 2, the anti-stain barrier 32 comprises two portions 32A and 32B, a longitudinal edge of each portion being joined to each of the longitudinal edges of the rewet barrier 22. Preferably, the disposable cover 20 also has absorbent securement means 41 disposed on the inwardly oriented surface of each portion of the anti-stain barrier 32 and garment securement means 43 disposed on the outwardly oriented surface 34 of the anti-stain barrier 32. The securement means 41, 43 hold the absorbent material 10 and the disposable cover 20 in place.

FIG. 2 is a plan view of the disposable cover 20 of the present invention in its flat-out state with the portion of the disposable cover 20 which faces or contacts the user, the outwardly oriented surface 24 of the rewet barrier 22, oriented towards the viewer. The disposable cover 20 has two centerlines, a longitudinal centerline 100 and a transverse centerline 102. The term "longitudinal", as used herein, refers to a line, axis or direction in the plane of the disposable cover 20 that is generally aligned with (e.g., approximately parallel to) a vertical plane which bisects a standing user into left and right body halves when the disposable 20 is worn. The terms "transverse" or "lateral" as used herein, are interchangeable, and refer to a line, axis or direction which lies within the plane of the disposable cover 20 that is generally perpendicular to the longitudinal direction. As also can be seen in FIG. 2, the disposable cover 20 comprises two components, a liquid pervious rewet barrier 22 for reducing liquid contact with the skin and a liquid impervious anti-stain barrier 32 for reducing the risk of soiling a user's garments.

As shown in FIG. 2, the rewet barrier 22 has two surfaces, an outwardly oriented surface 24, at least a portion of which surface contacts the user's body, and an inwardly oriented surface 26, a portion of which surface faces, and preferably contacts, contacts the absorbent material 10. That portion of the rewet barrier 22 which can contact a user's body for transport of liquids, such as the portion between the stiffening members 42, is referred to herein as the transport region 25. The disposable cover 20 is shown in FIG. 1 and 2 as viewed from the outwardly oriented surface 24 of the rewet barrier 22. The outwardly oriented surface 24 is intended to be worn adjacent to the body of the user while the inwardly oriented surface 26 is on the opposite side of the rewet barrier 22. A portion of the inwardly oriented surface 26 is intended to be placed adjacent the absorbent material 10. The remainder of the inwardly oriented surface of the rewet barrier 22 contacts the anti-stain barrier 32 to form the stiffening member 42. The rewet barrier 22 has a pair of longitudinally oriented side edges 28 and 29.

In the simplest embodiment of the disposable cover 20, the disposable cover 20 can comprise only a rewet barrier 22. Such a simple embodiment can be wrapped around an absorbent material 10. When the disposable cover 20 comprises only a rewet barrier 22, the surface area of such a disposable cover 20 should be comparable to surface area of the preferred embodiment of the disposable cover 20 discussed herein. That is, the length dimension of such a simple disposable cover 20 should be comparable to the length dimension I discussed hereinbelow and the width dimension of such a simple disposable cover 20 should be comparable to the sum of the width dimensions $w_1$, $w_2$, and $w_3$ discussed hereinbelow. Such a simple disposable cover can also be provided with attachment means as discussed hereinbelow.

Such a simple embodiment of the present invention provides many of the desirable benefits of the preferred embodiment of the disposable cover 20. Specifically, when such an embodiment is used with a folded cloth absorbent material, the combination provides improved skin dryness. This embodiment also reduces the tendency for folding configuration changes and undesirable shape changes (e.g. when the absorbent material 10 comprises a tow of fibers or wadding). This latter benefit is believed to result in improved absorbency and reduced leakage.

An alternative simple embodiment of the disposable cover 20 comprises an anti-stain barrier 32 disposed between the absorbent material 10 and the wearer's garments. Such an embodiment would reduce staining of a wearer's garments by reducing transfer of bodily fluids from the absorbent material 10 to the garments. This embodiment of the present invention should be sized such that a portion of the absorbent material 10 is not covered by the anti-stain barrier 32 to allow transport of bodily fluids into the absorbent material 10. This uncovered portion of the absorbent material serves the same purpose as the transport region 25 of the preferred embodiment of the present invention that is shown in FIG. 2. Thus, the length dimension of this simple embodiment of the disposable cover 20 should be comparable to the length dimension 1 discussed below and the width dimension of such a simple disposable cover 20 should provide for the uncovered portion of the absorbent material 10. Since such an embodiment cannot be wrapped entirely around the absorbent material 10, if a portion of the absorbent material is to remain uncovered, means to secure the anti-stain barrier 32 to the absorbent material 10 are required. Such absorbent securement means are disposed on that surface of the anti-stain barrier 32 which contacts the absorbent material 10, preferably such means are centered between the longitudinal edges of the disposable wrapper 20. This simple embodiment of the disposable cover 20 may also comprise means for attaching the assembly of the disposable wrapper 20 and the absorbent material 10 to a wearer's undergarments. Suitable materials for this simple embodiment are essentially the same as those suitable for the preferred embodiment of the present invention shown in FIG. 2. Such materials are discussed in greater detail below.

Preferably, however, the disposable cover 20 of the present invention comprises both a rewet barrier 22 and an anti-stain barrier 32. The anti-stain barrier 32 may be joined to the rewet barrier 22 along one of the longitudinally oriented side edges 28, 29 thereof. In the preferred embodiment of the present invention shown in FIG. 2, the anti-stain barrier 32 comprises two portions, a first portion 32A joined to longitudinal edge 29 of the rewet barrier 22 and a second portion 32B joined to longitudinal edge 28 of the rewet barrier 22. Because of the symmetry of the portions, like elements of each portion are described with the same reference number with a reference letter A or B to indicate the respective portions. As is also shown in FIG. 2, each portion of the anti-stain barrier 32 has two surfaces, an outwardly oriented surface 34A, 34B, respectively, a portion of which outwardly oriented surface contacts the user's undergarment, and an inwardly oriented surface 36A, 36B, respectively, a portion of which inwardly oriented surface contacts the absorbent material 10 when the disposable cover 20 is used. Each portion of the anti-stain barrier 32 also has a pair of longitudinally oriented side edges 38A, 38B and 39A, 39B, respectively.

Figure 3:
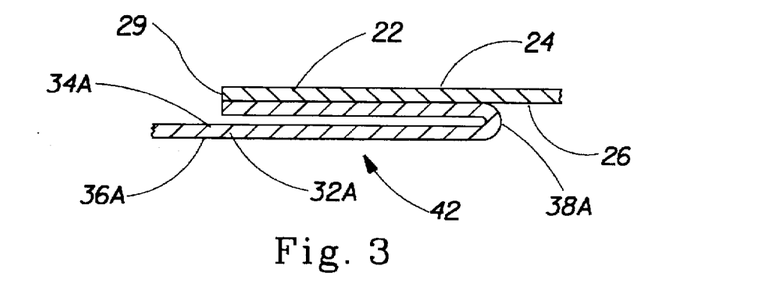
FIG. 3 is an enlarged cross section of the disposable cover of the present invention taken along line 3—3.

FIG. 3 shows a cross section of the disposable cover 20 taken along line 3—3. As is shown in FIG. 3, the rewet barrier 22 and the anti-stain barrier 32 are preferably joined in regions along at least one of their longitudinal edges.

The rewet barrier 22 and the anti-stain barrier 32 are joined to each other by attachment means (not shown) such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In the preferred embodiment of the present invention, the rewet barrier 22 and the anti-stain barrier 32 are joined directly to each other. For example, the rewet barrier 22 and the anti-stain barrier 32 may be secured to each other by an adhesive. The adhesive can be in the form of a uniform continuous layer of adhesive, a patterned layer of adhesive, or an array of separate lines, spirals, or spots of adhesive. Exemplary adhesive attachment are disclosed in U.S. Pat. No. 4,573,986 issued to Minetola, et al. on Mar. 4, 1986; U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Preferably, the attachment means joining the rewet barrier 22 and the anti-stain barrier 32 comprises at least one seam formed by the application of pressure, with or without added heat, commonly referred to as a crimp seam. Alternatively, the attachment means may comprise heat bonds, ultrasonic bonds, dynamic mechanical bonds, or any other suitable attachment means or combinations of these attachment means as are known in the art.

Alternatively, the rewet barrier 22 and the anti-stain barrier 32 that are joined to form the disposable cover 20 of the present invention can comprise a single material (for example, a single sheet of material). In such an embodiment, a first portion of the material is liquid pervious and the remaining portions of the material are liquid impervious. For example, capillaries could be provided to a central portion of an, otherwise, liquid impervious material. When the disposable cover 20 comprises a single material, the surface area of such a disposable cover 20 should be comparable to the surface area of the preferred embodiment of the disposable cover 20 discussed herein. That is, the length dimension of such a simple disposable cover 20 should be comparable to the length dimension 1 discussed hereinbelow and the width dimension of such a simple disposable cover 20 should be comparable to the sum of the width dimensions w1, w2, and w3 discussed hereinbelow. Also, the surface area of the individual liquid pervious and liquid impervious portions of the single material embodiment should be comparable to the surface area of the corresponding separate materials. That is, the surface area of the liquid pervious portion should be comparable to the surface area of the rewet barrier 22 and the surface area of the liquid impervious portion should be comparable to the anti-stain barrier 32. This embodiment of the disposable cover 20 can also be provided with attachment means as discussed hereinbelow.

As is also shown in FIG. 3, the disposable cover 20 of the present invention preferably also comprises a stiffening member 42 located adjacent each longitudinal edge 28, 29 of the liquid pervious rewet barrier 22. The stiffening member 42 provides a preferential fold line defining the transport region 25 of the rewet barrier 22. The stiffening member 42 also provides additional structure adjacent the edges of the transport region 25 that can resist bunching of the absorbent material and, thus, reduce lateral leakage of bodily fluids.

The disposable cover 20 can also comprise absorbent securement means 41 which holds the absorbent material 10 in place with respect to the disposable cover 20 and garment securement means 43 which serves to hold the assembly comprising the disposable cover 20 of the present invention and an absorbent material 10 in a desired location in a user's garments. In the preferred embodiment shown in FIGS. 1 and 2, the absorbent securement means 41 is disposed adjacent both longitudinal edges 39A and 39B on the inwardly oriented surface 36A, 36B of the anti-stain barrier 32. The garment securement means 43 is disposed adjacent one of the longitudinal edges 39A or 39B on the outwardly oriented surface 34A or 34 B of the anti-stain barrier 32, for example, in the strip configuration shown in FIG. 2. While the securement means 41, 43 are not critical to the functionality of the disposable cover 20, providing such means increases the reliability of the performance of the disposable cover 20 because it is more likely to remain in a proper orientation with respect to the absorbent material 10 and a user's body.

The absorbent material 10 can comprise any absorbent means which is capable of absorbing or retaining bodily liquids (e.g., menses and/or urine). As shown in FIG. 1, the absorbent material 10 has a body surface 11 and a garment surface 13. The absorbent material 10 can be manufactured in a wide variety of sizes and shapes and from a wide variety of liquid-absorbent materials commonly used in sanitary napkins and other absorbent articles such as nonwoven fabrics, tissue, and comminuted wood pulp (which is generally referred to as airfelt). The absorbent material 10 can also comprise other materials that are capable of absorbing and retaining liquids such as woven cloth, tows of fibers (natural, synthetic or combinations thereof), other similar materials that may be generally used to absorb and retain bodily liquids in developing countries, and the like.

Liquid Pervious Rewet Barrier Of The Disposable Cover

The liquid pervious rewet barrier 22 can be manufactured in a wide variety of sizes and shapes (e.g., rectangular, oval, asymmetric, etc.). In the preferred embodiment of the present invention shown in FIG. 2, the rewet barrier 22 has a thin rectangular sheet-like configuration. Preferably, the length 1 of the liquid pervious sheet is between about 150 mm and about 310 mm, more preferably the length 1 is about 280 mm. The width $w_2$ of the rewet barrier is preferably between about 60 mm and about 120 mm, more preferably the width $w_2$ is about 90 mm.

A suitable liquid pervious rewet barrier 22 may be manufactured from a wide range of materials such as woven and nonwoven materials; polymeric materials such as apertured formed thermoplastic films, apertured plastic films, and hydroformed thermoplastic films; porous foams; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred liquid pervious rewet barrier 22 comprises an apertured formed film. Apertured formed films are preferred for the liquid pervious rewet barrier 22 because they are pervious to body exudates yet non-absorbent and, if properly apertured, have a reduced tendency to allow liquids to pass back through and rewet a user's skin. Thus, the surface of the formed film which is in contact with the body remains dry, thereby reducing body soiling and creating a more comfortable feel for the user. A preferred liquid pervious rewet barrier 22 comprises an apertured formed film having tapered apertures each having a base in the outwardly oriented surface 24 and an apex in the inwardly oriented surface 26. Another preferred liquid pervious rewet barrier 22 for the present invention is the formed film marketed on sanitary napkins by the Procter & Gamble Company of Cincinnati, Ohio as "DRI-WEAVE". Suitable formed films are described in U.S. Pat. No. 3,929,135 which issued to Thompson on Dec. 30, 1975; U.S. Pat. No. 4,324,246 which issued to Mullane, et al. on Apr. 13, 1982; U.S. Pat. No. 4,342,314 which issued to Radel, et al. on Aug. 3, 1982; U.S. Pat. No. 4,463,045 entitled which issued to Ahr, et al. on Jul. 31, 1984; and U.S. Pat. No. 5,006,394 issued to Baird on Apr. 9, 1991. Each of these patents is incorporated herein by reference.

In a preferred embodiment of the present invention, the outwardly oriented surface 24 of the liquid pervious rewet barrier 22 is hydrophilic so as to help liquid to transfer through the rewet barrier 22 faster than if the outwardly oriented surface 24 was not hydrophilic so as to diminish the likelihood that bodily liquids will flow off the disposable cover 20 rather than being transported through the cover and being absorbed by the absorbent material 10. In a preferred embodiment, surfactant is incorporated into the polymeric materials of the formed film such as is described in U.S. Pat. No. 4,950,264, which issued to Osborn on Aug. 21, 1990, which is incorporated herein by reference. Alternatively, the outwardly oriented surface 24 of the disposable cover 20 can be made hydrophilic by treating it with a surfactant such as is also described in the above referenced U.S. Pat. No. 4,950,264.

The rewet barrier 22, or portions thereof, can also be provided with laterally oriented stretch as described hereinbelow with respect to the anti-stain barrier 32. For example, such laterally oriented stretch would be useful for providing the simple disposable cover comprising only a rewet barrier 22 discussed above with the added benefits of fitting a wider range of folded configurations for the absorbent material 10 and of applying, if the rewet barrier 22 comprises an elasticized material, a confining pressure to the absorbent material 10.

Liquid Impervious Anti-stain Barrier Of The Disposable Cover

The anti-stain barrier 32 is at least liquid resistant, and is preferably impervious to bodily liquids (e.g., menses and/or urine). the anti-stain barrier 32 is preferably manufactured from a thin plastic film, although other flexible liquid impervious materials may also be used. As used herein, the term "flexible" refers to materials which are compliant and will readily conform to the general shape and contours of the human body. The anti-stain barrier 32 prevents the exudates absorbed and contained in the absorbent material 10 from wetting articles which contact the sanitary napkin 20 such as pants, pajamas and undergarments. The anti-stain barrier 32 may thus comprise a woven or nonwoven material, polymeric films such as thermoplastic films of polyethylene or polypropylene, or composite materials such as a film-coated nonwoven material. Preferably, the anti-stain barrier 32 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The anti-stain barrier 32 is preferably embossed and/or matte finished to provide a more clothlike appearance. Further, the anti-stain barrier 32 may permit vapors to escape from the absorbent material 10 (i.e., breathable) while still preventing exudates from passing through the anti-stain barrier 32.

The liquid impervious anti-stain barrier 32 can be manufactured in a wide variety of sizes and shapes (e.g., rectangular, oval, asymmetric, etc.). In a preferred embodiment of the present invention, the liquid impervious anti-stain barrier 32 comprises two portions 32A and 32B each having a rectangular, thin, sheet-like configuration. The length 1 of each portion 32A and 32B is at preferably least about 200 mm, more preferably the length ranges from about 250 mm to 310 mm, and most preferably the length 1 is about 280 mm. The width $w_1$, $w_3$ of each portion is at preferably least about 50 mm, more preferably the width of each portion ranges from about 50 mm to 70 mm, and most preferably the width $w_1$, $w_3$ of each portion is about 60 mm.

The liquid impervious anti-stain barrier 32, or portions thereof, can also be provided with laterally oriented stretch. Such laterally oriented stretch allows the disposable cover 20 of the present invention to wrap around a wider range of folded configurations for the absorbent material 10 than would be possible if such stretch were not provided. Laterally oriented stretch also can apply a confining pressure to the absorbent material 10 if the anti-stain barrier 32 comprises an elasticized material.

Non-elastic laterally oriented stretch can be provided to the anti-stain barrier 32 by using materials having a low Young's modulus (i.e. materials that can be stretched past their yield value by the application of a low applied force) therefor. Alternatively, the anti-stain barrier 32 can comprise an elasticized material. For example, the anti-stain barrier 32 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the copending, commonly assigned U.S. Pat. No. 5,518,801, issued in the name of Chappell, et. al. on May 21, 1996 which is incorporated herein by reference. Alternatively, a stretchable anti-stain barrier 32 can comprise an elastomeric film such as that described in U.S. Pat. No. 4,476,180, issued to Wnuk on Oct. 9, 1984. Such a film is manufactured by Exxon Chemical Company, Lake Zurich, Ill., under the designation EXX500.

Stiffening Member of the Disposable Cover

The stiffening member 42 provides a region that is at least slightly stiffer than the other regions of the disposable cover 20. As can be seen in FIG. 1, this additional stiffness tends to cause the rewet barrier 22 and the anti-stain barrier 32 to preferentially fold about the stiffening member 42 defining the longitudinal edges of transport region 25. The stiffness also provides additional structure adjacent the longitudinal edges of the transport region 25 that is believed to provide some resistance to the undesirable compression of the absorbent material 10 due to the lateral forces exerted by the inside of a user's legs known as "bunching". Depending on the lateral width of the absorbent material 10, the stiffening member 42 can also act as a barrier to the lateral flow of liquids past the longitudinal edges of the transport region 25.

The stiffening member 42 can comprise one or more of the components of the disposable cover 20. Alternatively, it can comprise a separate component such as a foam that is joined to one or both of the components of the disposable cover 20. The radiation crosslinked polyethylene foams sold by Voltek, Inc. of Lawrence, Mass. under the trade name Volara is an example of a foam material that would be suitable as a stiffening member 42. Preferably, as is shown in FIGS. 2 and 3, the stiffening member 42 comprises solely elements of the disposable cover 20 that are folded, secured, or otherwise configured to provide the disposable cover 20 with a stiffened region. As is most clearly shown in FIG. 3, a portion of the film that forms the anti-stain barrier 32A is folded about itself in a c-fold to form a longitudinal edge 38A of the anti-stain barrier 32A. In a preferred embodiment, the folded portion of the film forming the anti-stain barrier 32 can be joined (means not shown) to the underlying portion of the film (i.e. to itself). This can be done using means essentially the same as those used to join the rewet barrier 22 to the anti-stain barrier 32. As is also shown in FIG. 3, the longitudinal edge 29 of the rewet barrier 22 extends laterally past longitudinal edges 38A of the anti-stain barrier 32A to provide additional stiffness to the stiffening member 42. The rewet barrier 22 is preferably joined to the anti-stain barrier 32A as described above. Similar folding and joinder can be used to provide a second stiffening member 42 using portions of anti-stain barrier 32B and rewet barrier 22 on the other side of the disposable cover 20.

Securement Means of the Disposable Cover

The disposable cover 20 can also comprise absorbent securement means 41 which holds the absorbent material 10 in place with respect to the disposable cover 20 and garment securement means 43 which serves to hold the assembly comprising the disposable cover 20 of the present invention and an absorbent material 10 in a desired location in a user's garments. Absorbent securement means 41 is used to attach the disposable cover 20 to the absorbent material 10. As can be seen from FIG. 2, the absorbent securement means 41 is disposed on the inwardly facing surface 36A, 36B of both portions of the anti-stain barrier 32 adjacent the longitudinal edges 39A and 39B thereof. The absorbent securement means 41 may also be disposed at other locations on the inwardly facing surface 36 depending on the specific design of the disposable cover 20 as long as such means is capable of attaching the disposable cover 20 to an absorbent material 10. Garment securement means 43 is used to attach the assembly comprising an absorbent material 10 and the disposable cover 20 to a user's undergarment. Garment securement means 43 can be disposed on one or both of the outwardly facing surfaces 34A or 34B of the portions of the anti-stain barrier 32 adjacent to the longitudinal edge 39A or 39B thereof (shown in FIG. 2 disposed on outwardly facing surface 34A). If desired, depending on the specific design of the disposable cover 20, garment securement means 43 may also be disposed on the outwardly facing surface 24 of the rewet barrier 22 along a longitudinally oriented side edge 28, 29 thereof. Preferably, the securement means 41, 43 comprise a fastener such as an adhesive. In a preferred embodiment of the present invention, the liquid impervious anti-stain barrier 32 is coated with adhesive to form the securement means 41, 43. Exemplary adhesives are Century A-305-IV manufactured by the Century Adhesives Corporation of Columbus, Ohio; and Instant Lock 34-2823 manufactured by the National Starch and Chemical Company of Bridgewater, N.J. Before the disposable cover 20 is placed in use, the adhesive is typically covered with a removable release liner in order to keep the adhesive from drying out or adhering to a surface other than the surface for which it is intended. Non-limiting examples of suitable release liners are BL30MG-A Silox E1/0 and BL30MG-A Silox 4P/O both of which are manufactured by the Akrosil Corporation of Menasha, Wis. Alternatively, the securement means 41, 43 can comprise a mechanical fastening means such as a hook and loop fastening means or other means known to those skilled in the art.

The securement means 41, 43 may be manufactured in a wide variety of sizes and shapes (e.g., rectangular, asymmetric, continuous, intermittent, etc.). In the preferred embodiment of the present invention shown in FIG. 2, the securement means 41, 43 comprise a narrow strip configuration. The area of this strip can vary as desired for controlling the degree of attachment. In the preferred embodiment shown in FIG. 2, the strips have a width of from about 5 mm to about 30 mm and a length of about 150 mm to about 250 mm. Preferably, the strips have a width of about 20 mm and a length of about 180 mm.

The above described disposable cover 20 is easily applied to an absorbent material 10 to provide a catamenial system.

For example, when the absorbent material 10 comprises a portion of folded, woven cloth, the user centers the absorbent material 10 on the inwardly oriented surface 26 of the rewet barrier 22. The release liner is removed from the adhesive comprising the absorbent attachment means 41 and each portion 32A and 32B is folded about the absorbent material 10 and removably attached thereto. Alternatively, the user can overlap the longitudinal edges 39A, 39B and use a portion of the absorbent attachment means 41 to join the two portions of the anti-stain barrier 32 to provide an improved barrier against leakage of adsorbed bodily fluids. The user can then remove the release liner from the adhesive comprising the garment attachment means, locate the assembly in her undergarment, insuring that the disposable cover is removably attached thereto, and pull the undergarment on in the normal manner. After the user has determined that the absorbent material has reached its capacity for absorbing bodily liquids, the catamenial system can be readily removed from the undergarment, the disposable cover 20 can be easily separated from the absorbent material 10 and disposed of in an environmentally friendly manner, and the absorbent material can be laundered according to the user's normal practices.

Alternative Embodiments of the Disposable Cover

Figure 4:
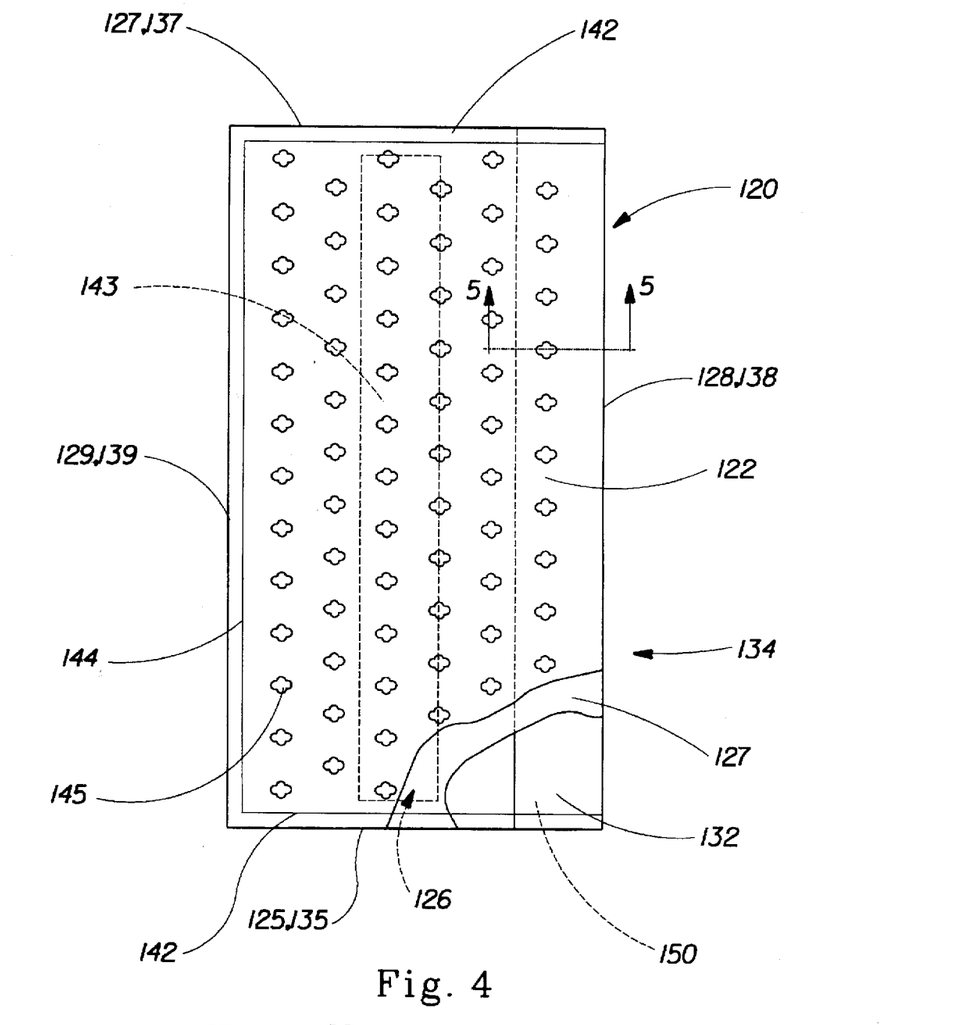
FIG. 4 is a plan view of a first alternative embodiment of the disposable cover of the present invention, a covering pouch, having portions cut away to show underlying structure.

FIG. 4 shows a first alternative embodiment of the disposable cover of the present invention, a covering bag or pouch 120 that would be suitable for use with absorbent materials 10, such as a tow of fibers, that have less structural integrity than a woven cloth. As can be seen from FIG. 4, the covering pouch 120 also comprises a liquid pervious rewet barrier 122 and a liquid impervious anti-stain barrier 132 as described hereinabove. The rewet barrier 122 has two surfaces, an outwardly oriented surface 124, a portion of which surface contacts the user's body, and an inwardly oriented surface 126, a portion of which surface faces the absorbent material, two end edges 125, 127 and two longitudinal edges 128, 129. Similarly, the anti-stain barrier 132 has two surfaces, an outwardly oriented surface 134, a portion of which surface contacts the user's undergarments, and an inwardly oriented surface 136, a portion of which surface contacts the absorbent material, two end edges 135, 137 and two longitudinal edges 138, 139. The length and width dimensions of the covering pouch 120 can vary to meet the specific needs of groups of users. However, preferred embodiments of the covering pouch 120 will have essentially the same length and width dimensions as the rewet barrier 22 of the preferred embodiment of the present invention described hereinabove, the disposable cover 20.

Figure 5:
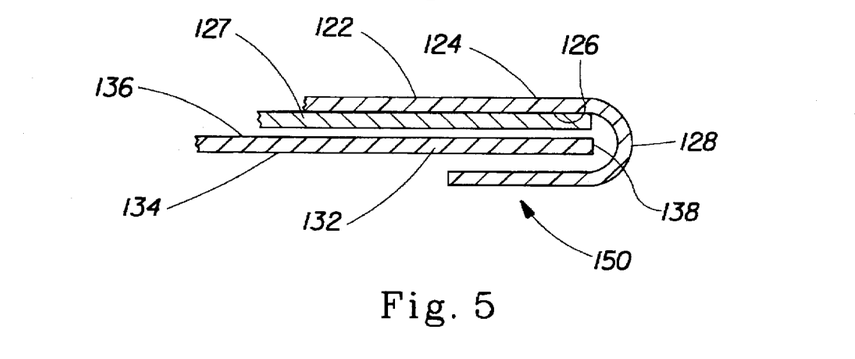
FIG. 5 is an enlarged cross section of the covering pouch of the present invention taken along line 5—5.

In the embodiment shown in FIGS. 4 and 5, a portion of the rewet barrier 122 extends beyond longitudinal edge 138 of the anti-stain barrier 132. That is, the lateral width of the material forming the rewet barrier 122 is greater than the lateral width of the material forming the anti-stain barrier 132. This extended material is folded about longitudinal edge 138 in a c-fold and joined only along end seams 142 to form closure flap 150. Alternatively, the extended portion of the rewet barrier 122 can be folded toward the outwardly facing surface 124 of the rewet barrier 122 in a c-fold and joined thereto only along end seams 142 to form closure flap 150. Those skilled in the catamenial products art will recognize that, if the portion of the rewet barrier that extends beyond longitudinal edge 138 is not c-folded and joined as described above, it may be tucked under the anti-stain barrier 132 by a user.

The rewet barrier 122 and the anti-stain barrier 132 are joined using means commonly known in the art, such as those discussed hereinabove. They are joined along both pairs of end edges 125, 135 and 127, 137 to form laterally oriented end seams 142 along each end of covering pouch 120 and along the longitudinal edge 129, 139 that lies opposite closure flap 150 to form longitudinal seam 144. Preferably, the means joining the rewet barrier 122 and the anti-stain barrier 132 comprises a seam formed by the application of pressure, with or without heat, commonly referred to as a crimp seam.

The covering pouch embodiments of the present invention preferably further comprise an acquisition layer 127 positioned between the rewet barrier 122 and the absorbent material 10. Such an acquisition layer 127 is shown in FIGS. 4 and 5. As can be seen therein, the acquisition layer extends the full longitudinal length of the covering pouch 120 and extends laterally between the side edges 128 and 129 of the rewet barrier 122. The acquisition layer 127 may serve several functions including improving wicking of exudates over and into the absorbent material 10. Improved wicking of exudates is important because it provides a more even distribution of the exudates throughout the absorbent material 10 (The wicking referred to herein may encompass the transportation of liquids in one, two or all directions (i.e., in the x-y plane and/or in the z-direction). The acquisition layer 127 may also resist projection of individual fibers of the absorbent material 10 through the fewer barrier 122 to the outwardly oriented surface 124 thereof, thereby reducing fewer potential (such projecting fibers can provide a reverse flow path through the rewet barrier 122 for absorbed bodily fluids).

As is shown FIGS. 4 and 5, the acquisition layer 127 is disposed on the inwardly oriented surface 126 of the rewet barrier 122 and extends longitudinally for the full length of the covering pouch 120 and laterally between the edges 128 and 129 of the rewet barrier 122. Alternatively, the acquisition layer 127 can be disposed on both the inwardly oriented surface 126 of the rewet barrier 122 and on the inwardly oriented surface 136 of the anti-stain barrier 132. In the embodiment shown in FIG. 4, the acquisition layer 127 and the rewet barrier 122 are preferably secured in at least partial contact with each other. The acquisition layer 127 and the rewet barrier 122 can be maintained in contact with each other by fusion bonding (including thermal bonding, ultrasonic bonding, crimping, and the like), adhesive attachment, or by any other securement means which does not interfere with wicking of exudates over and into the absorbent material 10. Most preferably, the acquisition layer 127 and the rewet barrier 122 are spot bonded at a plurality of spaced apart locations 145 by thermal bonds. One skilled in the catamenial products art would also recognize that acquisition layers similar to the one described herein would also be suitable for use in the disposable cover embodiments of the present invention that is discussed above.

The acquisition layer 127 may be comprised of different materials including, but not limited to, nonwoven or woven webs of synthetic fibers including polyester, polypropylene, or polyethylene; natural fibers including cotton or cellulose; blends of such fibers; or any equivalent materials or combinations of materials. Preferably, the acquisition layer 127 comprises a nonwoven material having a basis weight between about 8 pounds per 3000 square feet (10 grams per square yard-gsy) and about 30 pounds per 3000 square feet (45 gsy). More preferably, the basis weight of the nonwoven material is between about 10 pounds per 3000 square feet (12.5 gsy) and about 20 pounds per 3000 square feet (25 gsy). An example of such a nonwoven material is the spunbonded, hydrophobic nonwoven material having a basis weight of about 11 pounds per 3000 square feet (14 gsy)

which is known as Celestra, and is produced by Fiberweb, Noah America, Inc. of Simpsonville, N.C. Alternatively, the acquisition layer 127 can comprise a web of the relatively low density paper known as tissue having similar basis weights. Catamenial devices having an acquisition layer 127 and a rewet barrier 122 are more fully described in U.S. Pat. No. 4,950,264 issued to Osborn III on Aug. 21, 1990 and in U.S. patent application Ser. No. 07/810,774 filed Dec. 17, 1991 in the names of Cree, et al. Each of these references is incorporated herein by reference.

If desired, the covering pouch 120 can also comprise garment securement means 143 similar to those described hereinabove. The design of covering pouch 120 makes securement means similar to absorbent securement means 41 unnecessary.

To use the covering pouch 120, a user would take an absorbent material 10, such as a portion of a tow of fibers and insert it into the pouch between the rewet barrier 122 and the anti-stain barrier 132. The user then smoothes closure flap 150 to insure that the absorbent material 10 is securely contained in the covering pouch 120. If the covering pouch 120 also comprises securement means 143, any release liner covering the same is removed and the covering pouch 120 is secured to the user's undergarment as described hereinabove. The user can then pull on her undergarment in the normal manner.

Figure 6:
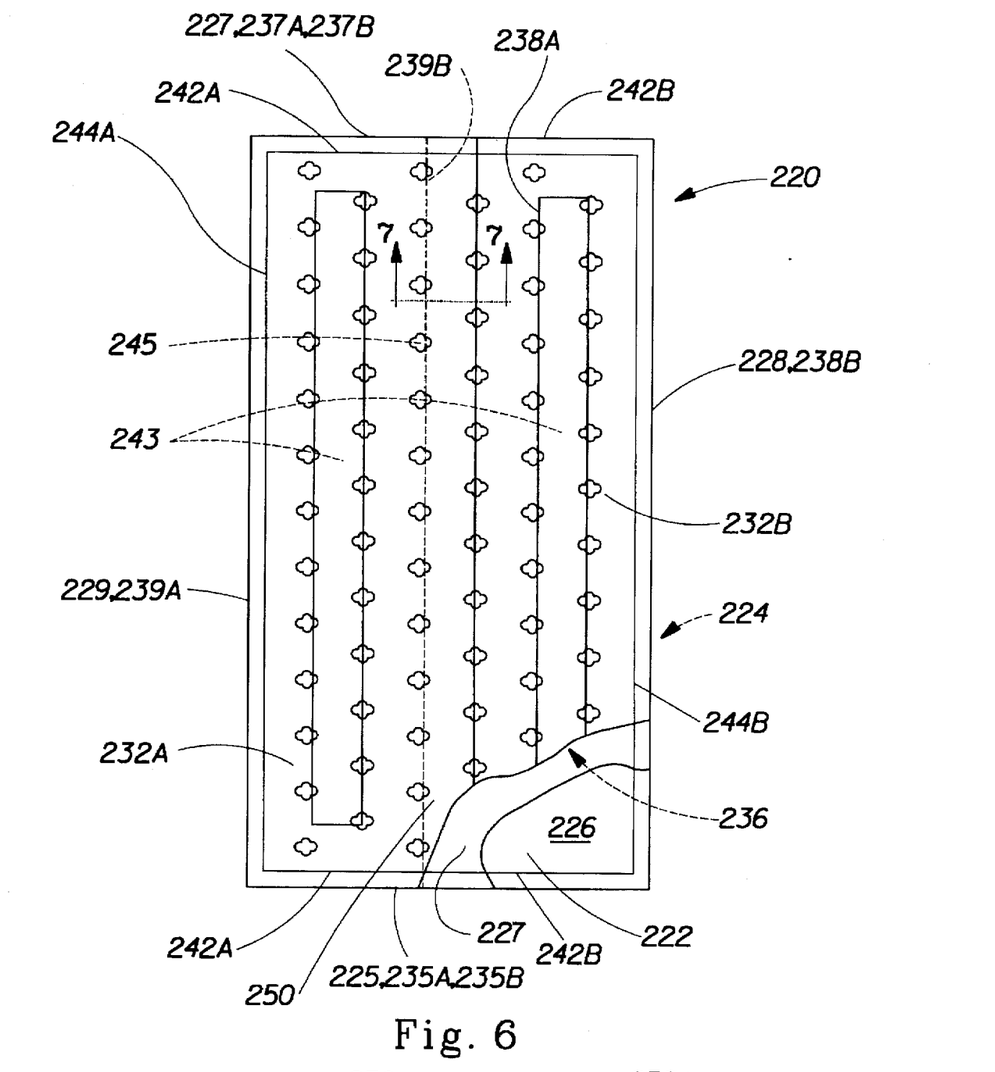
FIG. 6 is a plan view of a second alternative embodiment of the disposable cover of the present invention, an alternative covering pouch having portions cut away to show underlying structure the surface facing the viewer being the surface facing a user's garments.
Figure 7:
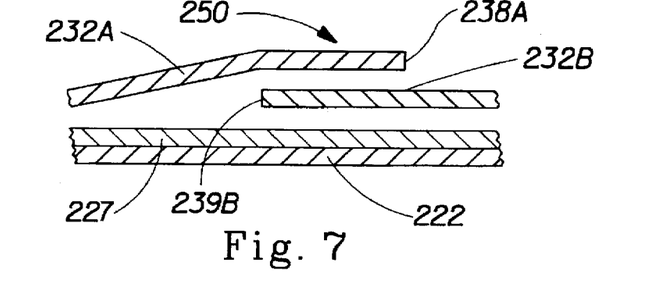
FIG. 7 is an enlarged cross section of the alternative covering pouch of the present invention taken along line 7—7.

Covering pouch 220, shown in FIGS. 6 and 7, is similar to covering pouch 120 except that the closure flap 250 thereof is located in approximately the center of the anti-stain barrier 232. This embodiment has the advantage that less of the relatively more expensive rewet barrier material is used than in the embodiment shown in FIGS. 4 and 5. As is clear from examination of FIGS. 6 and 7, the elements of covering pouch 220 that are equivalent to elements of covering pouch 120 have similar reference numbers. That is, fewer barrier 222 corresponds to rewet barrier 122; anti-stain barrier 232 corresponds to anti-stain barrier 132; and so forth. As can be seen in FIGS. 6 and 7, anti stain barrier 232 is provided in two portions 232A and 232B. Each edge of the rewet barrier 222 is joined to the corresponding edge of the anti-stain barrier 232. That is end edge 225A is joined to end edge 235A to form one of the end seams 242A; end edge 225B is joined to end edge 235B to form one of the end seams 242B; end edge 227A is joined to end edge 237A to form the other of the end seams 242A; end edge 227B is joined to end edge 237B to form the other of the end seams 242B; longitudinal edge 228 is joined to longitudinal edge 238B to form longitudinal seam 244B; and longitudinal edge 229 is joined to longitudinal edge 239A to form longitudinal seam 244A. As is most clearly shown in FIG. 7, longitudinal edge 238A overlaps longitudinal edge 239B forming closure flap 250. Covering pouch 220 can have the same dimensions and is used in essentially the same manner as covering pouch 120.

Covering pouch 220 may also comprise an acquisition layer 227 and garment securement means 243 as described hereinabove.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable cover for wrapping an absorbent material, said disposable cover comprising:

a liquid impervious anti-stain barrier which prevents liquids from penetrating its thickness, said anti-stain barrier having a first surface, at least a portion of said first surface contacting said absorbent material when said cover is wrapped about said absorbent material, an opposed second surface, and first and second longitudinally oriented side edges;

absorbent securement means disposed on said first surface, said absorbent securement means comprising an adhesive material with a release liner disposed thereon; and garment securement means disposed on said second surface along said first and second longitudinally oriented side edges.

2. A disposable cover for containing an absorbent material, said disposable cover being in pouch form and comprising:

a liquid impervious anti-stain barrier which prevents liquids from penetrating its thickness, said anti-stain barrier having a first surface at least a portion of which faces said absorbent material when said pouch contains said absorbent material and an opposed second surface, first and second end edges, and first and second longitudinally oriented side edges; and a liquid pervious rewet barrier which permits liquids to readily penetrate through its thickness, said rewet barrier having a first surface at least a portion of which faces said absorbent material when said pouch contains said absorbent material and an opposed second surface, first and second end edges, and first and second longitudinally oriented side edges, said rewet barrier having capillaries penetrating through said rewet barrier to permit flow of fluid from said second surface, through said rewet barrier, to said first surface wherein said rewet barrier overlies said anti-stain barrier and is joined to said anti-stain barrier along said first and second end edges of said anti-stain barrier and along said first side edge of said anti-stain barrier forming said pouch, said rewet barrier extending laterally beyond said second longitudinal edge of said anti-stain barrier, said anti-stain barrier and said rewet barrier being unattached along said second side edge of said anti-stain barrier providing an opening for insertion of said absorbent material into said pouch; and absorbent securement means disposed on said first surface of the anti-stain barrier, said absorbent securement means comprising an adhesive material with a release liner disposed thereon.

3. The disposable cover of claim 2 wherein said extension of said rewet barrier is folded about said second longitudinal edge of said anti-stain barrier and joined to said anti-stain barrier along said first and second end edges thereof.

4. The disposable cover of claim 2 wherein said extension of said rewet barrier is folded such that it overlies said portion of said rewet barrier which overlies said anti-stain barrier and is joined thereto along said first and second end edges.

5. A disposable cover for containing an absorbent material, said disposable cover having a lateral width, being in pouch form, and comprising:

a liquid impervious anti-stain barrier which prevents liquids from penetrating its thickness, said anti-stain barrier having a first surface at least a portion of which faces said absorbent material when said pouch contains said absorbent material and an opposed second surface, said anti-stain barrier comprising first and second portions, each portion having first and second end edges, first and second longitudinal edges, and a lateral width, wherein the lateral width of said first portion is greater than half the lateral width of said disposable cover; and a liquid pervious rewet barrier which permits liquids to readily penetrate through its thickness, said rewet barrier having a first surface at least a portion of which faces said absorbent material when said pouch contains said absorbent material and an opposed second surface, first and second end edges, and first and second longitudinally oriented side edges, said rewet barrier having capillaries penetrating through said rewet barrier to permit flow of fluid from said second surface, through said rewet barrier, to said first surface, wherein:

said second longitudinal edge of said second portion is joined to said second longitudinal edge of said rewet barrier;

said first end edge of said second portion is joined to said first end edge of said rewet barrier;

said second end edge of said second portion is joined to said second end edge of said rewet barrier;

said first longitudinal edge of said first portion is joined to said first longitudinal edge of said rewet barrier;

said first end edge of said first portion is joined to said first end edge of said rewet barrier;

said second end edge of said first portion is joined to said second end edge of said rewet barrier; and part of said first portion overlies said second portion, said overlying portion being unattached thereto and providing an opening for insertion of said absorbent material into said pouch; and absorbent securement means disposed on said first surface of the anti-stain barrier, said absorbent securement means comprising an adhesive material with a release liner disposed thereon.

6. The disposable cover of claim 5 wherein said disposable cover further comprises an acquisition layer disposed on and joined to said inwardly oriented surface of said rewet barrier.

7. The disposable cover of claim 6 wherein said disposable cover further comprises an acquisition layer disposed on and joined to said inwardly oriented surface of said anti-stain barrier.

8. A disposable cover for wrapping an absorbent material, said disposable cover comprising:

a liquid pervious rewet barrier which permits liquids to readily penetrate through its thickness, said rewet barrier having a first surface, at least a portion of said first surface contacting said absorbent material when said cover is wrapped about said absorbent material, an opposed second surface, and first and second longitudinally oriented side edges, said rewet barrier having tapered capillaries penetrating through said rewet barrier to permit flow of liquids from said second surface, through said fewer barrier, to said first surface;

a liquid impervious anti-stain barrier which prevents liquids from penetrating its thickness, said anti-stain barrier comprising first and second portions, each portion having a first surface, at least a portion of said first surface contacting said absorbent material when said cover is wrapped about said absorbent material, an opposed second surface, and first and second longitudinally oriented side edges;

first and second stiffening members, each of said stiffening members having first and second longitudinally oriented side edges, wherein said second side edge of said first stiffening member is joined to said first side edge of said rewet barrier, said first side edge of said first stiffening member is joined to said second side edge of said first portion of said anti-stain barrier, said first side edge of said second stiffening member is joined to said second side edge of said rewet barrier, and said second side edge of said second stiffening member is joined to said second side edge of said second portion of said anti-stain barrier wherein a difference in stiffness between each of said stiffening member and each of said portions of said anti-stain barrier defines a preferential fold line between said rewet barrier and said anti-stain barriers; and absorbent securement means disposed on said first surface of the anti-stain barrier, said absorbent securement means comprising an adhesive material with a release liner disposed thereon.

9. The disposable cover of claim 8 further comprising the absorbent securement means disposed on said first surface of each of said portions of said anti-stain barrier adjacent said first edge of each of said portions.

10. The disposable cover of claim 8 further comprising garment securement means disposed on said outwardly oriented surface of said anti-stain barrier adjacent said first side edge of said first portion.

11. The disposable cover of claim 8 wherein the anti-stain barrier is elastically extensible in the lateral direction.

12. A disposable cover for wrapping an absorbent material, said disposable cover having a first surface, at least a portion of said first surface contacting said absorbent material when said cover is wrapped about said absorbent material, an opposed second surface, and a pair of longitudinally oriented side edges, said disposable cover comprising:

a liquid pervious rewet barrier which permits liquids to readily penetrate through its thickness, said rewet barrier having capillaries penetrating through said rewet barrier to permit flow of fluid from said second surface, through said rewet barrier, to said first surface;

absorbent securement means disposed onto said first surface adjacent each of said side edges so as to secure said cover to said absorbent material said absorbent securement means comprising an adhesive; and a release liner disposed on said adhesive.

13. The disposable cover of claim 12 wherein said capillaries comprise tapered apertures each having a base in said second surface and an apex in said first surface.

14. The disposable cover of claim 12 wherein said securement means comprises an adhesive.

15. The disposable cover of claim 12 wherein said cover further comprises a stiffening member joined to said rewet barrier adjacent at least one of said side edges.

16. The disposable cover of claim 12 wherein said cover is elastically extensible in the lateral direction.

17. A disposable cover for wrapping an absorbent material, said disposable cover comprising:

a liquid pervious rewet barrier which permits liquids to readily penetrate through its thickness, said fewer barrier having a first surface, at least a portion of said first surface contacting said absorbent material when said cover is wrapped about said absorbent material, an opposed second surface, first and second end edges, and first and second longitudinally oriented side edges, said rewet barrier having capillaries penetrating through said rewet barrier to permit flow of fluid from said second surface, through said rewet barrier, to said first surface; and a liquid impervious anti-stain barrier which prevents liquids from penetrating its thickness, said anti-stain barrier having a inwardly oriented first surface, at least a portion of said first surface contacting said absorbent material when said cover is wrapped about said absorbent material, an opposed second surface, first and second end edges, and first and second longitudinally oriented side edges;

a longitudinally extending stiffening member having first and second longitudinally oriented side edges, said first edge of said stiffening member being joined to said first longitudinal edge of said rewet barrier and said second edge of said stiffening member being joined to said second longitudinal edge of said anti-stain barrier wherein a difference in stiffness between said stiffening member and said anti-stain barrier defines a preferential fold line between said rewet barrier and said anti-stain barrier; and at least a portion of the first surface contacting said absorbent material of the anti-stain barrier when said cover is wrapped about said absorbent material having securement means disposed thereon, said absorbent securement means comprising an adhesive material with a release liner disposed thereon.

18. The disposable cover of claim 17 wherein said capillaries comprise tapered apertures each having a base on said outwardly oriented surface and an apex on said inwardly oriented surface.

19. The disposable cover of claim 17 wherein said anti-stain barrier further comprises a second portion having first and second longitudinally oriented side edges, wherein said first side edge of said second portion of said anti-stain barrier is joined to said second side edge of said rewet barrier.

20. The disposable cover of claim 17 further comprising a garment securement means disposed on said second surface of said anti-stain barrier for securing the disposable cover to a wearer's garments.

21. The disposable cover of claim 17 wherein said securement means comprises an adhesive.

22. The disposable cover of claim 17 wherein said securement means comprises a mechanical fastener.

23. The disposable cover of claim 17 wherein said stiffening member comprises portions of said rewet barrier and said anti-stain barrier, wherein:

a portion of said anti-stain barrier is folded about itself along a longitudinally oriented fold line in a c-fold defining a folded portion, said folded portion of said anti-stain barrier defining the transverse width of said stiffening member; said second surface of said folded portion of said anti-stain barrier is joined to said second surface of that portion of said anti-stain barrier which it overlies; and a portion of said rewet barrier overlies said folded portion of said anti-stain barrier forming an overlying portion, said overlying portion of said rewet barrier being joined to said folded portion of anti-stain barrier to form said stiffening member.

24. The disposable cover of claim 17 wherein said disposable cover further comprises an acquisition layer disposed on and joined to said inwardly oriented surface of said rewet barrier.

25. The disposable cover of claim 24 wherein said disposable cover further comprises an acquisition layer disposed on and joined to said inwardly oriented surface of said anti-stain barrier.

* * * * *

UNITED STATES PATENT AND TRADEMARK OFFICE
CERTIFICATE OF CORRECTION

PATENT NO. : 5,688,258
DATED : November 18, 1997
INVENTOR(S) : Digvijay Rawat et al.

It is certified that error appears in the above-identified patent and that said Letters Patent is hereby corrected as shown below:

Title page,
Title of the Invention, "MATERIALS" should read -- MATERIAL --.
ABSTRACT, line 10, "fewer" should read -- rewet --.

Column 3,
Line 33, "fewer" should read -- rewet --.

Column 13,
Line 36, "fewer" should read -- rewet --.

Column 15,
Line 56, "fewer" should read -- rewet --.

Column 16,
Line 58, "fewer" should read -- rewet --.

Signed and Sealed this

Twelfth Day of March, 2002

Attest:

JAMES E. ROGAN
Director of the United States Patent and Trademark Office

Attesting Officer